(12) United States Patent
Maa et al.

(10) Patent No.: US 12,036,332 B2
(45) Date of Patent: Jul. 16, 2024

(54) GERMICIDAL LIGHTING APPARATUS WITH VISIBLE GLARE

(71) Applicant: Aleddra Inc., Renton, WA (US)

(72) Inventors: Chia-Yiu Maa, Bellevue, WA (US); Chun-Te Yu, Bellevue, WA (US)

(73) Assignee: Aleddra Inc., Renton, WA (US)

( * ) Notice: Subject to any disclaimer, the term of this patent is extended or adjusted under 35 U.S.C. 154(b) by 420 days.

(21) Appl. No.: 17/665,817

(22) Filed: Feb. 7, 2022

(65) Prior Publication Data

US 2022/0152255 A1    May 19, 2022

Related U.S. Application Data

(63) Continuation-in-part of application No. 17/499,775, filed on Oct. 12, 2021, which is a continuation-in-part of application No. 17/140,673, filed on Jan. 4, 2021, now abandoned, which is a continuation-in-part of application No. 17/137,763, filed on Dec. 30, 2020, now abandoned, which is a continuation-in-part of application No. 17/099,271, filed on Nov. 16, 2020, now abandoned.

(51) Int. Cl.
*A61L 2/24* (2006.01)
*A61L 2/08* (2006.01)
*A61L 2/10* (2006.01)

(52) U.S. Cl.
CPC ............. *A61L 2/24* (2013.01); *A61L 2/084* (2013.01); *A61L 2/10* (2013.01)

(58) Field of Classification Search
CPC .............. A61L 2/24; A61L 2/084; A61L 2/10
See application file for complete search history.

(56) References Cited

U.S. PATENT DOCUMENTS

| 2022/0152232 A1* | 5/2022 | Maa | H05B 47/115 |
| 2022/0152236 A1* | 5/2022 | Maa | A61L 2/084 |
| 2022/0152239 A1* | 5/2022 | Maa | A61L 2/24 |
| 2022/0152253 A1* | 5/2022 | Maa | A61L 2/24 |

* cited by examiner

*Primary Examiner* — Nicole M Ippolito
*Assistant Examiner* — Hanway Chang
(74) *Attorney, Agent, or Firm* — Han IP PLLC; Andy M. Han

(57) ABSTRACT

A germicidal lighting apparatus with visible glare includes a first light source, a second light source, a first driver, a second driver, and a controller. The first light source emits a light in a 180~280 nm wavelength range and the second light source emits a light in a visible wavelength range greater than 400 nm. The second light source is positioned adjacent to the first light source and serves as a visible glare source to deter an occupant from looking at the apparatus directly. The controller can turn on both the first light source and the second light source simultaneously to produce a unified glare rating (UGR) greater than 16. The apparatus dispenses over a prorated 8-hour period an irradiation dosage greater than American Conference of Governmental Industrial Hygienists (ACGIH)-specified Eye Threshold Limit Values (TLV) but less than ACGIH-specified Skin TLV to a substance or surface.

15 Claims, 5 Drawing Sheets

| Schedule | Operation Mode |
|---|---|
| 7:00am to 7:00pm | Safe sanitation |
| 7:00pm to 7:00am | Default mode: Full sanitation<br>Upon motion detection: Safe sanitation |

FIG. 3

GERMICIDAL LIGHTING APPARATUS WITH VISIBLE GLARE

CROSS REFERENCE TO RELATED PATENT APPLICATIONS

The present disclosure is a Continuation-in-Part (CIP) of U.S. patent application Ser. No. 17/499,775, filed 12 Oct. 2021, which is a CIP of U.S. patent application Ser. No. 17/140,673, filed 4 Jan. 2021, which is a CIP of U.S. patent application Ser. No. 17/137,763, filed 30 Dec. 2020, which is a CIP of U.S. patent application Ser. No. 17/099,271, filed on 16 Nov. 2020, the contents of which being incorporated by reference in their entirety.

BACKGROUND

Technical Field

The present disclosure pertains to germicidal lighting devices and, more specially, proposes a germicidal lighting apparatus with visible glare.

Description of Related Art

In the U.S. patent application Ser. No. 17/499,775, a germicidal irradiation apparatus was introduced. It includes a first light source, a second light source, a first driver, a second driver, and a controller. The first light source emits a light in a wavelength range of 190~280 nm. The second light source emits a light in a wavelength range of 315~420 nm. The first driver is configured to convert an external power to an internal power to activate the first light source, whereas second driver is configured to convert an external power to an internal power to activate the second light source. The controller is configured to turn on the first light source and the second light source individually or simultaneously.

The irradiation dosage of the germicidal irradiation apparatus presented in the U.S. patent application Ser. No. 17/499,775 was based on ACGIH (American Conference of Governmental Industrial Hygienists) specified Threshold Limit Values (TLV) that were published in ACGIH ISBN: 0-9367-12-99-6, 2007. These ACGIH TLV are plotted in the solid curve in FIG. 1, referred to as 2020 ACGIH TLV in the figure since they were use all through 2020. However, recent studies show the 2020 ACGIH TLV were too conservative. A higher irradiation tolerance could be administrated to human subjects without causing any damage. In 2021, ACGIH proposed new and higher TLVs. Additionally, ACGIH has identified the TLV for skin is higher than the TLV for eye for wavelengths less than 300 nm. The new ACGIH TLV for eye and skin are also plotted in FIG. 1. It can be seen from FIG. 1 that at 222 nm wavelength, there are a seven-fold increase on the TLV for eye from 22 mJ/cm² to 160 mJ/cm², and another three-fold increase to 479 mJ/cm² for skin (https://www.acgih.org/science/tlv-bei-guidelines/documentation-publications-and-data/notice-of-intended-changes/notice-of-intended-changes-list/).

Considering the new ACGIH TLVs for eye and skin, it would be reasonable to increase irradiation dosage administrated by the germicidal irradiation apparatus presented in the U.S. patent application Ser. No. 17/499,775 for a higher germicidal effect. The new ACGIH TLVs pose another question, however, that is too which level of TLV a germicidal irradiation apparatus should administrate. If an germicidal irradiation apparatus administrates the irradiation according to the new ACGIH Eye TLV, then it can be argued that it would not provide sufficient germicidal effectiveness to skins. Conversely, if the apparatus administrates the irradiation according to the new ACGIH Skin TLV, then it has the risk of causing irradiation overdosage for eyes.

The present disclosure proposes a germicidal lighting apparatus with visible glare so that it could administrate irradiation dosage above the new ACGIH Eye TLV while using its visible glare to deter an occupant from looking into the apparatus, thus avoiding irradiation overdosage to eyes while maximizing the germicidal effectiveness for skin and clothes of the occupant and the surrounding air and surfaces.

SUMMARY

In one aspect, the germicidal lighting apparatus comprises a first light source emitting a light in a 180~280 nm wavelength range, a second light source emitting a light greater than 400 nm, a first driver, a second driver, and a controller. The first light source is an ultraviolet-C (UVC) light source. The first driver is configured to convert an external power to a first internal power to activate the first light source, and the second driver is configured to convert an external power to a second internal power to activate the second light source. The second light source is positioned adjacent to the first light source and serves as a visible glare source to deter an occupant from looking at the apparatus directly. This is necessary because the first light source is a UVC light source emitting invisible wavelengths. Without a visible glare in the apparatus, an occupant may look at the apparatus accidentally for a long period of time and get an UV overdosage. The second light source provides a discomfort glare and thus steers the occupant away from staring at the apparatus. Moreover, the controller is configured to turn on both the first light source and the second light source simultaneously such that the apparatus may produce a unified glare rating (UGR) greater than 16. A UGR greater than 16 is chosen for it provides a sufficient discomfort glare, thus having the effect of deterring an occupant for looking at the apparatus directly and preventing the eyes of the occupant from UV overdosage. When the controller turns on both the first light source and the second light source simultaneously, the apparatus dispenses over a prorated 8-hour period an irradiation dosage greater than ACGIH-specified Eye TLV but less than ACGIH-specified Skin TLV to a substance or surface to be disinfected by the apparatus. Such irradiation dosage can be expressed in mathematical form as the following irradiation safety formula:

$$\sum_{K=180\ nm}^{280\ nm} \frac{\text{The received irradiation at the wavelength } K}{ACGIH \text{ Eye } TLV \text{ at the wavelength } K} > 100\% \text{ and}$$

$$\sum_{K=180\ nm}^{280\ nm} \frac{\text{The received irradiation at the wavelength } K}{ACGIH \text{ Skin } TLV \text{ at the wavelength } K} < 100\%.$$

The irradiation safety formula above considers the irradiation of all wavelengths in the range of 180~280 nm. In some embodiments, where the first light source has a first peak wavelength and a second peak wavelength in a range of 180~280 nm, and their combined irradiation dosage is over 95% of the total irradiation dosage of the first light source, the irradiation safety formula may be approximated by the following simplified irradiation safety formula:

$$\frac{\text{The received irradiation at 1st peak wavelength}}{ACGIH \text{ Eye } TLV \text{ at the 1st peak wavelength}} +$$
$$\frac{\text{The received irradiation at 2nd peak wavelength}}{ACGIH \text{ Eye } TLV \text{ at the 2nd peak wavelength}} > 100\%$$

and $$\frac{\text{The received irradiation at 1st peak wavelength}}{ACGIH \text{ Skin } TLV \text{ at the 1st peak wavelength}} +$$
$$\frac{\text{The received irradiation at 2nd peak wavelength}}{ACGIH \text{ Skin } TLV \text{ at the 2nd peak wavelength}} < 100\%$$

A good example is the KrCl excimer lamp having a first peak wavelength at 222 nm and a second peak wavelength at 257.5 nm as shown in FIG. 2. The irradiation at these to peak wavelengths far exceeds other wavelengths in the range 180~280 nm. It is easier to use the simplified irradiation safety formula on these two peak wavelengths for calculating the safe irradiation dosage of this embodiment.

When the first light source having two or more peak wavelengths, it is not uncommon to filter out the more harmful peak wavelengths (i.e., the peak wavelengths having lower ACGIH-specified TLVs) and use the irradiation of the remaining peak wavelength. In some embodiments, where the first light source has a first peak wavelength, and its irradiation dosage is over 95% of the total irradiation dosage of the first light source, the irradiation safety formula may be approximated by the following simplified irradiation safety formula:

$$\frac{\text{The received irradiation at 1st peak wavelength}}{ACGIH \text{ Eye } TLV \text{ at the 1st peak wavelength}} > 100\% \text{ and}$$
$$\frac{\text{The received irradiation at 1st peak wavelength}}{ACGIH \text{ Skin } TLV \text{ at the 1st peak wavelength}} < 100\%$$

When applying a low-pass filter to an KrCl excimer lamp with a cutoff frequency at 230 nm, this would permit only the first peak wavelength 222 nm to pass through, for the second peak wavelength 257.5 nm is blocked by the filter. Under such a scenario, the simplified irradiation safety formula on the first peak wavelength may be used for calculating the safe irradiation dosage of this embodiment.

In some embodiments, the controller is configured to support two operation modes: a safe sanitation mode and a full sanitation mode. The safe sanitation mode is meant to be used when occupants are in the space and the full sanitation mode is meant for off-hours operation when nobody is in the space. In the safe sanitation mode, the apparatus dispenses to the substance or surface to be disinfected by the apparatus over a prorated 8-hour period an irradiation dosage in compliance with the following irradiation safety formula:

$$\sum_{K=180\,nm}^{280\,nm} \frac{\text{The received irradiation at the wavelength } K}{ACGIH \text{ Eye } TLV \text{ at the wavelength } K} > 100\% \text{ and}$$

$$\sum_{K=180\,nm}^{280\,nm} \frac{\text{The received irradiation at the wavelength } K}{ACGIH \text{ Skin } TLV \text{ at the wavelength } K} < 100\%.$$

In the full sanitation mode, the apparatus dispenses to the substance or surface to be disinfected by the apparatus over a prorated 8-hour period an irradiation dosage in compliance with the following irradiation safety formula:

$$\sum_{K=180\,nm}^{280\,nm} \frac{\text{The received irradiation at the wavelength } K}{ACGIH \text{ Skin } TLV \text{ at the wavelength } K} > 100\%.$$

There are different configurations of the apparatus to support the safe sanitation model. For example, the controller may be configured to operate the apparatus in the safe mode less than 8 hours, e.g., for only 1 hours. However, so long the prorated dosage over 8 hours is less than ACGIH-specified Skin TLV, it is considered safe by ACGIH guidelines. Similarly, there are different configurations of the apparatus to support the full sanitation mode, so long as the dispensed UV dosage prorated over 8 hours to the substance or surface to be disinfected exceeds ACGIH-specified Skin TLV.

There are different means for triggering the controller to switch between the safe sanitation mode and the full sanitation mode. In some embodiments, the controller is configured to operate according to an operation schedule to toggle between the safe sanitation mode and the full sanitation mode. The operation schedule may be stored locally in the controller or remotely on a scheduling device or a lighting control system.

In some embodiments, the apparatus further comprises a motion sensor working in conjunction with the controller such that when a motion is detected by the motion sensor, the controller is configured to operate the apparatus in the safe sanitation mode, and when no motion is detected by the motion sensor, the controller is configured to operate the apparatus in the full sanitation mode. It is also possible for a controller to take into the account of both an operation schedule and the motion detection in setting the operation mode. FIG. 3 shows an example of such operation configuration. During 7:00 am to 7:00 pm, the controller operates the apparatus in the safe sanitation mode. Then from 7:00 pm to 7:am, the controller operates the apparatus in full sanitation mode by default. However, upon the defecting of motion, the controller will change temporarily to the safe sanitation mode, and later resumes the full sanitation mode when no further motion is detected in the space.

The disclosure thus far describes an aspect of the present disclosure which would dispense over a prorated 8-hour period an irradiation dosage greater than ACGIH-specified Eye TLV but less than ACGIH-specified Skin TLV to a substance or surface to be disinfected by the apparatus. There are however situations where a more conservative UV irradiation dosage is called for. For example, for a patient room in a hospital or in a dental clinic, a patient would often face up toward the ceiling. Under such circumstances, even the patent would not stare at the germicidal light apparatus mounted on the ceiling, the patient's eyes would still be fully exposed to the irradiation of the apparatus. It is necessary to use a more conservative UV irradiation dosage for germicidal lighting applications under these circumstances.

In another aspect of the present disclosure, the germicidal lighting apparatus comprises a first light source emitting a light in a 180~280 nm wavelength range, a second light source emitting a light greater than 400 nm, a first driver, a second driver, and a controller. The first driver is configured to convert an external power to a first internal power to activate the first light source, and the second driver is configured to convert an external power to a second internal power to activate the second light source. Moreover, the controller is configured to turn on both the first light source and the second light source simultaneously such that the apparatus may produce a UGR greater than 16, and the apparatus may dispense over a prorated 8-hour period an irradiation dosage greater than 50% of ACGIH-specified Eye TLV but less than 100% of ACGIH-specified Eye TLV to a substance or surface to be disinfected by the apparatus. This ensures the occupant's eyes will never be exposed to a UV irradiation dosage that exceeds the ACGIH-specified Eye TLV. Such irradiation dosage can be expressed in mathematical form as the following irradiation safety formula:

$$50\% < \sum_{K=180\,nm}^{280\,nm} \frac{\text{The received irradiation at the wavelength } K}{ACGIH \text{ Eye } TLV \text{ at the wavelength } K} < 100\%.$$

In some embodiments, where the first light source (e.g., a KrCl excimer lamp) has a first peak wavelength and a second peak wavelength in a range of 180~280 nm, and their combined irradiation dosage is over 95% of the total irradiation dosage of the first light source, the irradiation safety formula may be approximated by the following simplified irradiation safety formula:

$$50\% < \frac{\text{The received irradiation at 1st peak wavelength}}{ACGIH \text{ Eye } TLV \text{ at the 1st peak wavelength}} + \frac{\text{The received irradiation at 2nd peak wavelength}}{ACGIH \text{ Skin } TLV \text{ at the 2nd peak wavelength}} < 100\%$$

In some embodiments, where the first light source (e.g., a KrCl excimer lamp with a low-pass filter having a cutoff frequency at 230 nm) has a first peak wavelength, and its irradiation dosage is over 95% of the total irradiation dosage of the first light source, the irradiation safety formula may be approximated by the following simplified irradiation safety formula:

$$50\% < \frac{\text{The received irradiation at 1st peak wavelength}}{ACGIH \text{ Eye } TLV \text{ at the 1st peak wavelength}} < 100\%$$

In some embodiments, the controller is configured to support two operation modes: a safe sanitation mode and a full sanitation mode. In the safe sanitation mode, the apparatus dispenses to the substance or surface to be disinfected by the apparatus over a prorated 8-hour period an irradiation dosage in compliance with the following irradiation safety formula:

$$50\% < \sum_{K=180\,nm}^{280\,nm} \frac{\text{The received irradiation at the wavelength } K}{ACGIH \text{ Eye } TLV \text{ at the wavelength } K} < 100\%;$$

In the full sanitation mode, the apparatus dispenses to the substance or surface to be disinfected by the apparatus over a prorated 8-hour period an irradiation dosage in compliance with the following irradiation safety formula:

$$\sum_{K=180\,nm}^{280\,nm} \frac{\text{The received irradiation at the wavelength } K}{ACGIH \text{ Skin } TLV \text{ at the wavelength } K} > 100\%.$$

In some embodiments, the controller is configured to operate according to an operation schedule to toggle between the safe sanitation mode and the full sanitation mode. The operation schedule may be stored locally in the controller or remotely on a scheduling device or a lighting control system.

In some embodiments, the apparatus further comprises a motion sensor working in conjunction with the controller such that when a motion is detected by the motion sensor, the controller is configured to operate the apparatus in the safe sanitation mode, and when no motion is detected by the motion sensor, the controller is configured to operate the apparatus in the full sanitation mode. It is also possible for a controller to take into the account of both an operation schedule and the motion detection in setting the operation mode as illustrated by the operation schedule in FIG. 3.

The two aspects of the present disclosure described above (or in claims 1 and 7) use different irradiation safety formulas. It may be preferable to design a highly configurable controller such that for some application scenarios (e.g., general offices), the controller can be configured to use the following irradiation safety formula, $$\sum_{K=180\,nm}^{280\,nm} \frac{\text{The received irradiation at the wavelength } K}{ACGIH \text{ Eye } TLV \text{ at the wavelength } K} > 100\% \text{ and}$$

$$\sum_{K=180\,nm}^{280\,nm} \frac{\text{The received irradiation at the wavelength } K}{ACGIH \text{ Skin } TLV \text{ at the wavelength } K} < 100\%.$$

And for some other application scenarios (e.g., dental offices), the controller can be configured to use the following irradiation safety formula, $$50\% < \sum_{K=180\,nm}^{280\,nm} \frac{\text{The received irradiation at the wavelength } K}{ACGIH \text{ Eye } TLV \text{ at the wavelength } K} < 100\%.$$

Furthermore for some scenarios where a full sanitation is called for, the controller can be configured to use one of these following irradiation safety formulas, $$\sum_{K=180\,nm}^{280\,nm} \frac{\text{The received irradiation at the wavelength } K}{ACGIH \text{ Skin } TLV \text{ at the wavelength } K} > 100\%.$$

Thus, in another aspect of the present disclosure, the germicidal lighting apparatus comprises a first light source emitting a light in a 180~280 nm wavelength range, a second light source emitting a light greater than 400 nm, a first driver, a second driver, and a controller. The first driver is configured to convert an external power to a first internal power to activate the first light source and the second driver is configured to convert the external power to a second internal power to activate the second light source. The second light source is positioned adjacent to the first light source. The controller is configured to turn on both the first light source and the second light source simultaneously such that the apparatus may produce a UGR greater than 16. Moreover, the controller is configurable to support at least one of the following irradiation dosages to a substance or surface to be disinfected by the apparatus: 1) below the ACGIH-specified Eye TLV, 2) between ACGIH-specified Eye TLV and ACGIH-specified Skin TLV, and 3) above ACGIH-specified Skin TLV. With the controller being configurable on the irradiation dosage dispensed by the apparatus, a different irradiation dosage may be selected according to the application environment. For a general office environment, the controller may be configured such that the apparatus may dispense an irradiation dosage between ACGIH-specified Eye TLV and ACGIH-specified Skin TLV. For a dental office environment, the same controller may be configured such that the apparatus may dispense an irradiation dosage below ACGIH-specified Eye TLV. The controller may also be configured such that the apparatus may dispense a different irradiation dosage during different times of the day according to an operation schedule. Or the controller may be coupled with a motion sensor to toggle the irradiation of the apparatus between two different dosages based on whether a motion is detected by the motion sensor or not. Configuration of this highly configurable controller may be accomplished by a manual intervention of a user, or via a schedule stored locally in the controller, or a schedule stored remotely on an app or an irradiation dosage control system.

In yet another aspect of the present disclosure, the germicidal lighting apparatus comprises a first light source emitting a light in a 180~280 nm wavelength range, a second light source emitting a light greater than 400 nm, a first driver, and a second driver. The first driver is configured to convert an external power to a first internal power to activate the first light source and the second driver is configured to convert the external power to a second internal power to activate the second light source. The second light source is positioned adjacent to the first light source. The first light source and the second light source are configured to be turned on simultaneously such that the apparatus may produce a UGR greater than 16, and the apparatus dispenses a fixed irradiation dosage over a prorated 8-hour period to a substance or surface to be disinfected by the apparatus. The fixed irradiation may be 1) below the ACGIH-specified Eye TLV, or 2) between ACGIH-specified Eye TLV and ACGIH-specified Skin TLV, or 3) above ACGIH-specified Skin TLV. Note that the irradiation dosage dispensed by the apparatus is fixed since there is no controller adjusting the irradiation dosage. This aspect of the present disclosure may be considered an overly simplified and restricted case of claim 13 where the controller is reduced to a simple on/off switch. When the switch is turned on, both the first light source and the second light source are turned on for producing a UGR greater than 16 and emitting a fixed irradiation dosage.

In some embodiments, the apparatus further includes a motion sensor. The motion sensor controls the external power to the apparatus. When a motion is detected by the motion sensor, the first light source and the second light source are turned off. When no motion is detected by the motion sensor, the first light source and the second light source are turned on.

BRIEF DESCRIPTION OF THE DRAWINGS

The accompanying drawings are included to aid further understanding of the present disclosure, and are incorporated in and constitute a part of the present disclosure. The drawings illustrate a select number of embodiments of the present disclosure and, together with the detailed description below, serve to explain the principles of the present disclosure. It is appreciable that the drawings are not necessarily to scale, as some components may be shown to be out of proportion to size in actual implementation in order to clearly illustrate the concept of the present disclosure.

FIG. 3 shows an operation schedule example.

DETAILED DESCRIPTION OF PREFERRED EMBODIMENTS

Overview

Various implementations of the present disclosure and related inventive concepts are described below. It should be acknowledged, however, that the present disclosure is not limited to any particular manner of implementation, and that the various embodiments discussed explicitly herein are primarily for purposes of illustration. For example, the various concepts discussed herein may be suitably implemented in a variety of germicidal lighting apparatuses with visible glare having different form factors.

The present disclosure includes a first light source, a second light source, a first driver, a second driver, and a controller. The first light source emitting a light in a 180~280 nm wavelength range whereas the second light source emitting a light in a visible wavelength range greater than 400 nm. The second light source is positioned adjacent to the first light source. The controller is configured to turn on both the first light source and the second light source simultaneously such that the apparatus produces a UGR greater than 16, and the apparatus dispenses over a prorated 8-hour period an irradiation dosage greater than ACGIH-specified Eye TLV but less than ACGIH-specified Skin TLV to a substance or surface to be disinfected by the apparatus.

Example Implementations

Figure 1:
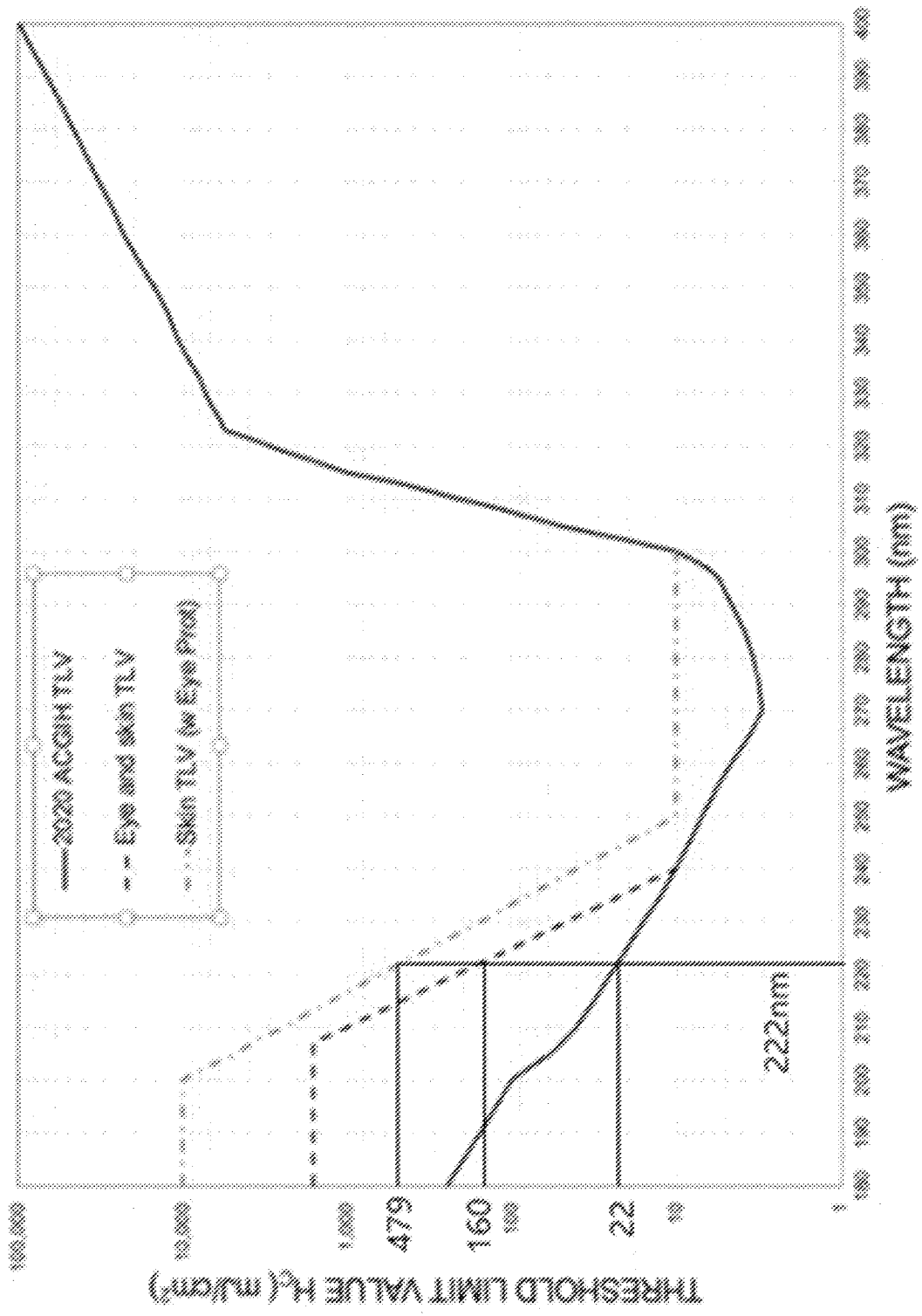
FIG. 1 The TLV dosage according to ACGIH UV Safety Guidelines.
Figure 2:
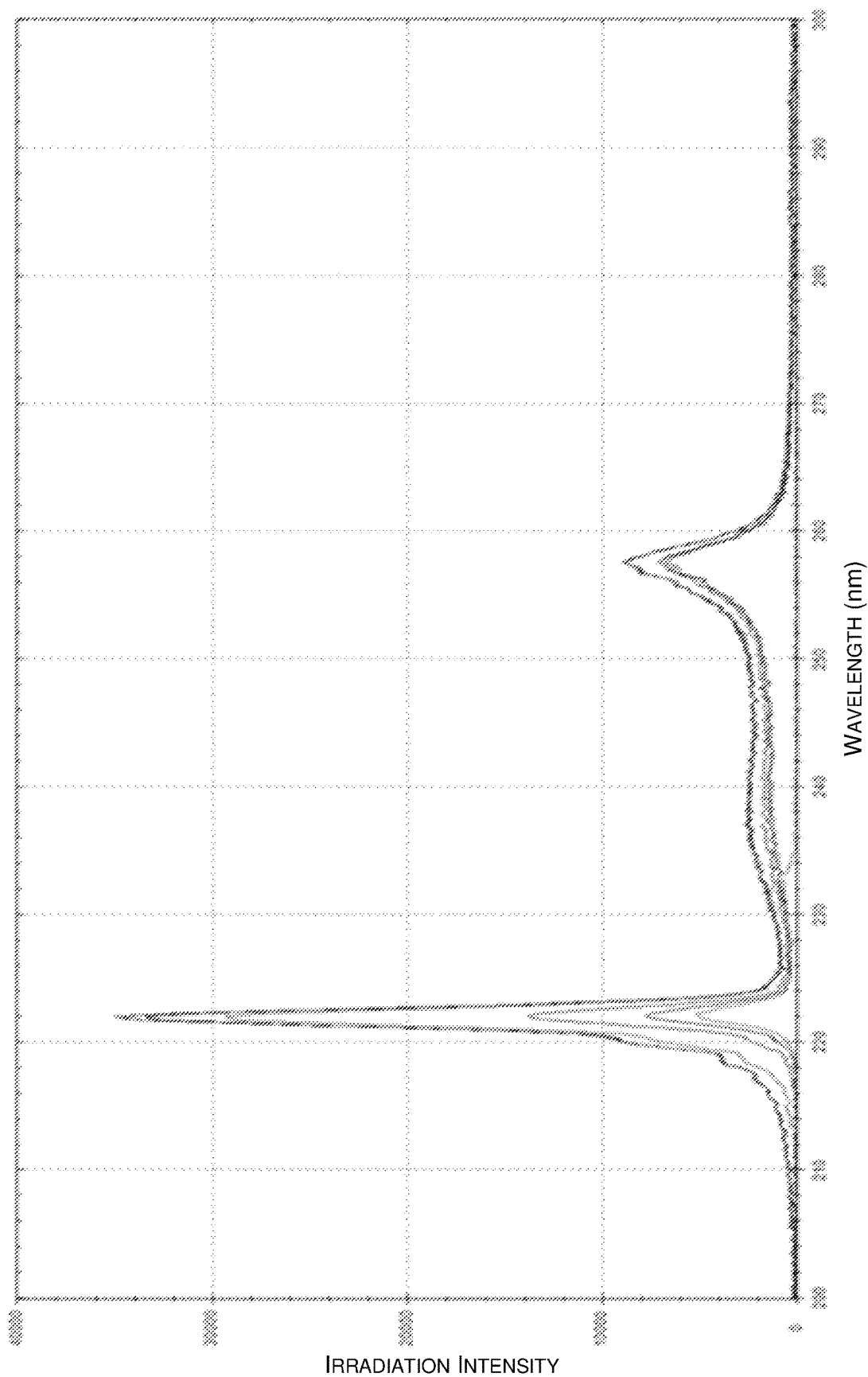
FIG. 2 shows the irradiation intensity of various KrCl excimer lamps.
Figure 4:
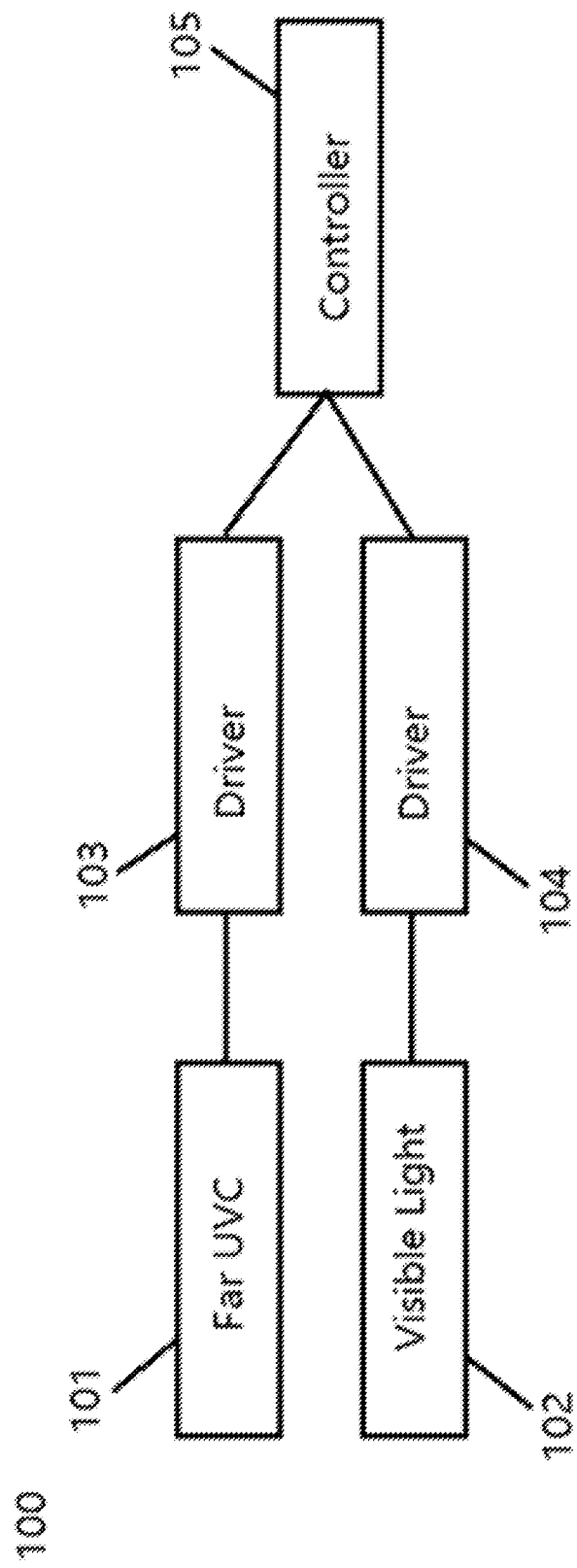
FIG. 4 schematically depicts a diagram of an embodiment of the present disclosure.

FIG. 4 is an embodiment of the germicidal lighting apparatus of the present disclosure. The apparatus 100 includes a far UVC light source 101 having a peak wavelength in a range of 180~280 nm, a visible light source 102, a first driver 103, a second driver 104, and a controller 105. The first driver 103 converts an external power to a first internal power for activating the far UVC light source 101, and the second driver 104 converts an external power to a second internal power for activating the visible light source 102. The controller 105 turns on the far UVC light source 101 and the visible light source 102 simultaneously and generates a UGR greater than 16. The far UVC light source 101 and the visible light source 102 are adjacent to each other. When an occupant looks at the apparatus or the far UVC light source 101, he/she inevitably feels the discomfort glare from the visible light source 102, thus turning his/her eyes away from the apparatus. The chances the eyes of the occupant being overexposed with UVC is thus avoided.

If this embodiment 100 is to be used in a regular office environment, the first and the second light sources and the controller may be selected and constructed such that this embodiment would dispense over a prorated 8-hour period an irradiation dosage greater than ACGIH-specified Eye TLV but less than ACGIH-specified Skin TLV to an occupant or a substance or a surface to be disinfected by the embodiment. Alternatively, if this embodiment is to be used in a dental office, then the first and the second light sources and the controller may be selected and constructed such that this embodiment would dispense over a prorated 8-hour period an irradiation dosage greater than 50% of ACGIH-specified Eye TLV but less than 100% of ACGIH-specified Eye TLV to an occupant or a substance or a surface to be disinfected by the embodiment.

For an application that would only need to provide a fixed irradiation, the embodiment 100 may be simplified by removing the controller and having the first driver 103 and the second driver 104 wired directly to one external power source such that the first light source 101 and the second light source 102 would be turned on at the same time with the first light source emitting a fixed irradiation.

Figure 5:
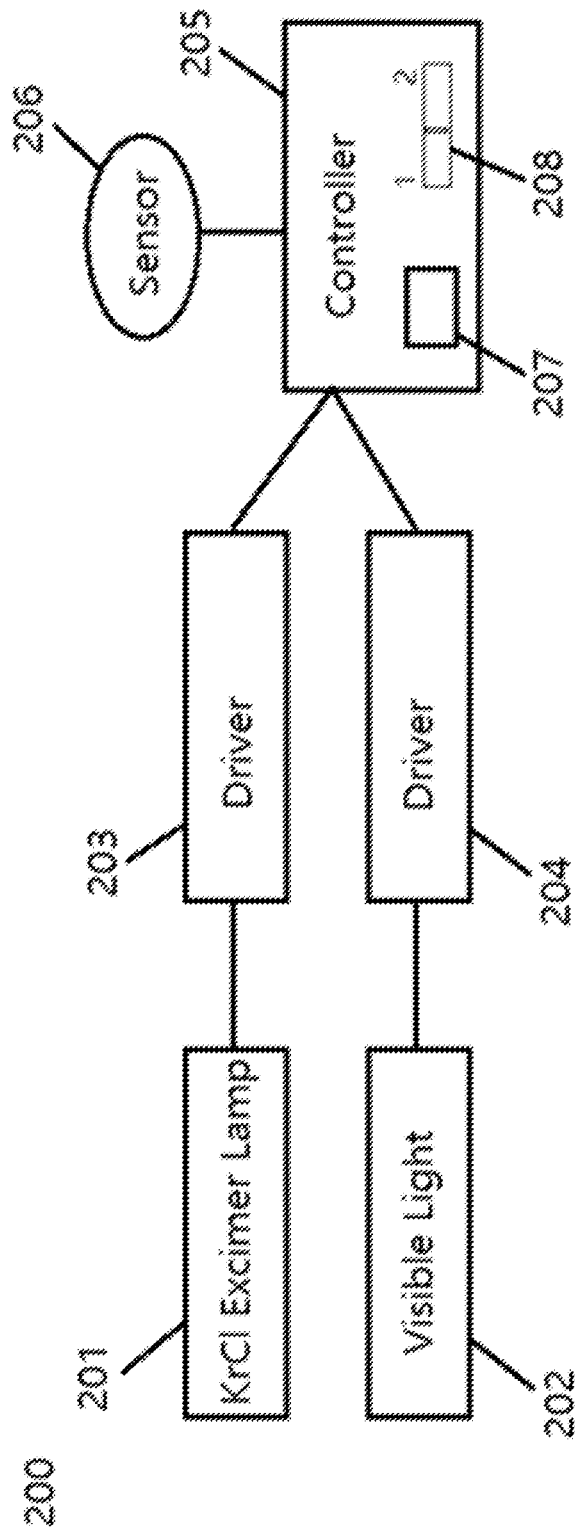
FIG. 5 schematically depicts a diagram of another embodiment of the present disclosure with a motion sensor.

FIG. 5 is another embodiment of the present disclosure 200. The apparatus 200 includes a KrCl excimer lamp 201, a visible light source 202, a first driver 203, a second driver 204, a controller 205, and a motion sensor 206. The KrCl excimer lamp 201 emits two peak wavelengths at 222 nm and 257.5 nm, and these two wavelengths contribute over 95% of the total irradiation of this embodiment. The controller 205 turns on the KrCl excimer lamp 201 and the visible light source 202 simultaneously, generating a UGR over 16. This embodiment supports two operation modes: the safe sanitation mode and the full sanitation mode. The controller 205 is highly configurable. If this embodiment is to be used in a regular office environment, the controller 205 is configured for such application by setting the configuration switch 208 to position 1. Then, in the safe sanitation mode, this embodiment would dispense over a prorated 8-hour period a total irradiation dosage (from 222 nm and 257.5 nm wavelengths) greater than ACGIH-specified Eye TLV but less than ACGIH-specified Skin TLV to an occupant or a substance or a surface to be disinfected by the apparatus. In the full sanitation mode, the embodiment dispenses over a prorated 8-hour period a total irradiation dosage (from 222 nm and 257.5 nm wavelengths) greater than ACGIH-specified Skin TLV to the occupant or substance or surface to be disinfected by the embodiment. The total irradiation dosage is the aggregate of the irradiations at 222 nm and 257.5 nm.

If this embodiment 200 is to be used in a dental office, the controller 205 is configured for such application by setting the configuration switch 208 to position 2. This is so that this embodiment would dispense over a prorated 8-hour period an irradiation dosage (from 222 nm and 257.5 nm wavelengths) greater than 50% of ACGIH-specified Eye TLV but less than 100% of ACGIH-specified Eye TLV to a substance or surface to be disinfected by the embodiment. In the full sanitation mode, the embodiment dispenses over a prorated 8-hour period an irradiation dosage (from 222 nm and 257.5 nm wavelengths) greater than ACGIH-specified Eye TLV to the occupant or substance or surface to be disinfected by the embodiment.

Additionally, this embodiment operates according to an operation schedule stored in a memory module 207 embedded in the controller 205. The operation schedule is shown in FIG. 3. During 7:00 am to 7:00 pm, the controller 307 operates this embodiment in the safe sanitation mode, regardless of the motion detection. During 7:00 pm to 7:00 am, the controller operates in the full sanitation mode by default. However, if a motion is detected by the motion sensor 206 during this period, the controller switches the operation to the safe sanitation mode temporarily, avoiding any occupant from being over-exposed to the UV light. When no further motions are detected by the motion sensor, the controller resumes the operation to the full sanitation mode.

Additional and Alternative Implementation Notes

Although the techniques have been described in language specific to certain applications, it is to be understood that the appended claims are not necessarily limited to the specific features or applications described herein. Rather, the specific features and examples are disclosed as non-limiting exemplary forms of implementing such techniques. As used in this application, the term "or" is intended to mean an inclusive "or" rather than an exclusive "or." That is, unless specified otherwise or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more," unless specified otherwise or clear from context to be directed to a singular form.

What is claimed is:

1. A germicidal lighting apparatus, comprising:
a first light source configured to emit a first wavelength in a range of 180~280 nm;
a second light source configured to emit a second wavelength greater than 400 nm;
a first driver;
a second driver; and
a controller,
wherein:
the first driver is configured to convert an external power to a first internal power to activate the first light source,
the second driver is configured to convert the external power to a second internal power to activate the second light source,
the second light source is positioned adjacent to the first light source, and
the controller is configured to turn on both the first light source and the second light source simultaneously such that:
the apparatus produces a unified glare rating (UGR) greater than 16, and
the apparatus dispenses over a prorated 8-hour period an irradiation dosage greater than an American Conference of Governmental Industrial Hygienists (ACGIH)-specified Eye Threshold Limit Value (TLV) but less than an ACGIH-specified Skin TLV to a substance or surface being disinfected by the apparatus, or equivalently as defined in an irradiation safety formula as follows with respect to an amount of irradiation received at the substance or surface at a wavelength K:

$$\sum_{K=180\ nm}^{280\ nm} \frac{\text{The received irradiation at the wavelength } K}{ACGIH \text{ Eye } TLV \text{ at the wavelength } K} > 100\% \text{ and}$$

$$\sum_{K=180\ nm}^{280\ nm} \frac{\text{The received irradiation at the wavelength } K}{ACGIH \text{ Skin } TLV \text{ at the wavelength } K} < 100\%.$$

2. The apparatus of claim 1, wherein the first light source has a first peak wavelength and a second peak wavelength in a range of 180~280 nm, wherein a combined irradiation dosage at the first and the second peak wavelengths is over 95% of a total irradiation dosage of the first light source, and wherein the irradiation safety formula is approximated by a simplified form as follows:

$$\frac{\text{The received irradiation at 1st peak wavelength}}{ACGIH \text{ Eye } TLV \text{ at the 1st peak wavelength}} +$$
$$\frac{\text{The received irradiation at 2nd peak wavelength}}{ACGIH \text{ Eye } TLV \text{ at the 2nd peak wavelength}} > 100\%$$

and $$\frac{\text{The received irradiation at 1st peak wavelength}}{ACGIH \text{ Skin } TLV \text{ at the 1st peak wavelength}} +$$
$$\frac{\text{The received irradiation at 2nd peak wavelength}}{ACGIH \text{ Skin } TLV \text{ at the 2nd peak wavelength}} < 100\%.$$

3. The apparatus of claim 1, wherein the first light source has a first peak wavelength in a range of 180~280 nm, wherein the irradiation dosage at the first peak wavelength is over 95% of a total irradiation dosage of the first light source, and wherein the irradiation safety formula is approximated by a simplified form as follows:

$$\frac{\text{The received irradiation at 1st peak wavelength}}{ACGIH \text{ Eye } TLV \text{ at the 1st peak wavelength}} > 100\% \text{ and}$$
$$\frac{\text{The received irradiation at 1st peak wavelength}}{ACGIH \text{ Skin } TLV \text{ at the 1st peak wavelength}} < 100\%.$$

4. The apparatus of claim 1, wherein the controller is configured to support two operation modes comprising a safe sanitation mode and a full sanitation mode such that:

in the safe sanitation mode, the apparatus dispenses over a prorated 8-hour period an irradiation dosage in compliance with an irradiation safety formula as follows:

$$\sum_{K=180\ nm}^{280\ nm} \frac{\text{The received irradiation at the wavelength } K}{ACGIH \text{ Eye } TLV \text{ at the the wavelength } K} > 100\% \text{ and}$$
$$\sum_{K=180\ nm}^{280\ nm} \frac{\text{The received irradiation at the wavelength } K}{ACGIH \text{ Skin } TLV \text{ at the the wavelength } K} < 100\%;$$

in the full sanitation mode, the apparatus dispenses over a prorated 8-hour period an irradiation dosage in compliance with another irradiation safety formula as follows:

$$\sum_{K=180\ nm}^{280\ nm} \frac{\text{The received irradiation at the wavelength } K}{ACGIH \text{ Skin } TLV \text{ at the the wavelength } K} > 100\%.$$

5. The apparatus of claim 4, wherein the controller is configured to operate according to an operation schedule to toggle between the safe sanitation mode and the full sanitation mode.

6. The apparatus of claim 4, further comprising:
a motion sensor coupled to and configured to operate in conjunction with the controller,
wherein:
when a motion is detected by the motion sensor, the controller is configured to operate the apparatus in the safe sanitation mode, and
when no motion is detected by the motion sensor, the controller is configured to operate the apparatus in the full sanitation mode.

7. A germicidal lighting apparatus, comprising:
a first light source configured to emit a first wavelength in a range of 180~280 nm;
a second light source configured to emit a second wavelength greater than 400 nm;
a first driver;
a second driver; and
a controller,
wherein:
the first driver is configured to convert an external power to a first internal power to activate the first light source,
the second driver is configured to convert the external power to a second internal power to activate the second light source,
the second light source is positioned adjacent to the first light source, and
the controller is configured to turn on both the first light source and the second light source simultaneously such that:
the apparatus produces a unified glare rating (UGR) greater than 16, and
the apparatus dispenses over a prorated 8-hour period an irradiation dosage greater than 50% of an American Conference of Governmental Industrial Hygienists (ACGIH)-specified Eye Threshold Limit Value (TLV) but less than 100% of an ACGIH-specified Eye TLV to a substance or surface being disinfected by the apparatus, or equivalently as defined in an irradiation safety formula as follows:

$$50\% < \sum_{K=180\ nm}^{280\ nm} \frac{\text{The received irradiation at the wavelength } K}{ACGIH \text{ Eye } TLV \text{ at the the wavelength } K} < 100\%.$$

8. The apparatus of claim 7, wherein the first light source has a first peak wavelength and a second peak wavelength in a range of 180~280 nm, wherein a combined irradiation dosage at the first and the second peak wavelengths is over 95% of a total irradiation dosage of the first light source, and wherein the irradiation safety formula is approximated by an irradiation safety formula as follows:

$$50\% < \frac{\text{The received irradiation at 1st peak wavelength}}{ACGIH \text{ Eye } TLV \text{ at the 1st peak wavelength}} +$$
$$\frac{\text{The received irradiation at 2nd peak wavelength}}{ACGIH \text{ Eye } TLV \text{ at the 2nd peak wavelength}} < 100\%.$$

9. The apparatus of claim 7, wherein the first light source has a first peak wavelength in a range of 180~280 nm, wherein the irradiation dosage at the first peak wavelength is over 95% of a total irradiation dosage of the first light source, and wherein the irradiation safety formula is approximated by an irradiation safety formula as follows:

$$50\% < \frac{\text{The received irradiation at 1st peak wavelength}}{ACGIH \text{ Eye } TLV \text{ at the 1st peak wavelength}} < 100\%.$$

10. The apparatus of claim 7, wherein the controller is configured to support two operation modes comprising a safe sanitation mode and a full sanitation mode such that:
in the safe sanitation mode, the apparatus dispenses over a prorated 8-hour period an irradiation dosage in compliance with an irradiation safety formula as follows:

$$50\% < \sum_{K=180\,nm}^{280\,nm} \frac{\text{The received irradiation at the wavelength } K}{ACGIH \text{ Eye } TLV \text{ at the the wavelength } K} < 100\%;$$

in the full sanitation mode, the apparatus dispenses over a prorated 8-hour period an irradiation dosage in compliance with an irradiation safety formula as follows:

$$\sum_{K=180\,nm}^{280\,nm} \frac{\text{The received irradiation at the wavelength } K}{ACGIH \text{ Skin } TLV \text{ at the the wavelength } K} > 100\%.$$

11. The apparatus of claim 10, wherein the controller is configured to operate according to an operation schedule to toggle between the safe sanitation mode and the full sanitation mode.

12. The apparatus of claim 10, further comprising:
a motion sensor coupled to and configured to operate in conjunction with the controller,
wherein:
when a motion is detected by the motion sensor, the controller is configured to operate the apparatus in the safe sanitation mode, and
when no motion is detected by the motion sensor, the controller is configured to operate the apparatus in the full sanitation mode.

13. A germicidal lighting apparatus, comprising:
a first light source configured to emit a first wavelength in a range of 180~280 nm;
a second light source configured to emit a second wavelength greater than 400 nm;
a first driver;
a second driver; and
a controller,
wherein:
the first driver is configured to convert an external power to a first internal power to activate the first light source,
the second driver is configured to convert the external power to a second internal power to activate the second light source,
the second light source is positioned adjacent to the first light source, and
the controller is configured to turn on both the first light source and the second light source simultaneously such that:
the apparatus produces a unified glare rating (UGR) greater than 16, and
the controller is configurable to support at least one of the following irradiation dosages to a substance or surface to be disinfected by the apparatus:
1) below an American Conference of Governmental Industrial Hygienists (ACGIH)-specified Eye Threshold Limit Value (TLV),
2) between the ACGIH-specified Eye TLV and an ACGIH-specified Skin TLV, and
3) above the ACGIH-specified Skin TLV.

14. A germicidal lighting apparatus, comprising:
a first light source configured to emit a first wavelength in a range of 180~280 nm;
a second light source configured to emit a second wavelength greater than 400 nm;
a first driver; and
a second driver;
wherein:
the first driver is configured to convert an external power to a first internal power to activate the first light source,
the second driver is configured to convert the external power to a second internal power to activate the second light source,
the second light source is positioned adjacent to the first light source, and
the first light source and the second light source are configured to be turned on simultaneously such that:
the apparatus produces a unified glare rating (UGR) greater than 16, and
the apparatus dispenses to a substance or surface to be disinfected by the apparatus over a prorated 8-hour period a fixed irradiation dosage.

15. The apparatus of claim 14, further comprising:
a motion sensor coupled to and configured to operate in conjunction with the controller,
wherein:
when a motion is detected by the motion sensor, the first light source and the second light source are turned off, and
when no motion is detected by the motion sensor, the first light source and the second light source are turned on.

* * * * *